Feb. 6, 1945. W. ARMACOST Plant Pat. 649
ROSE PLANT
Filed Oct. 17, 1944
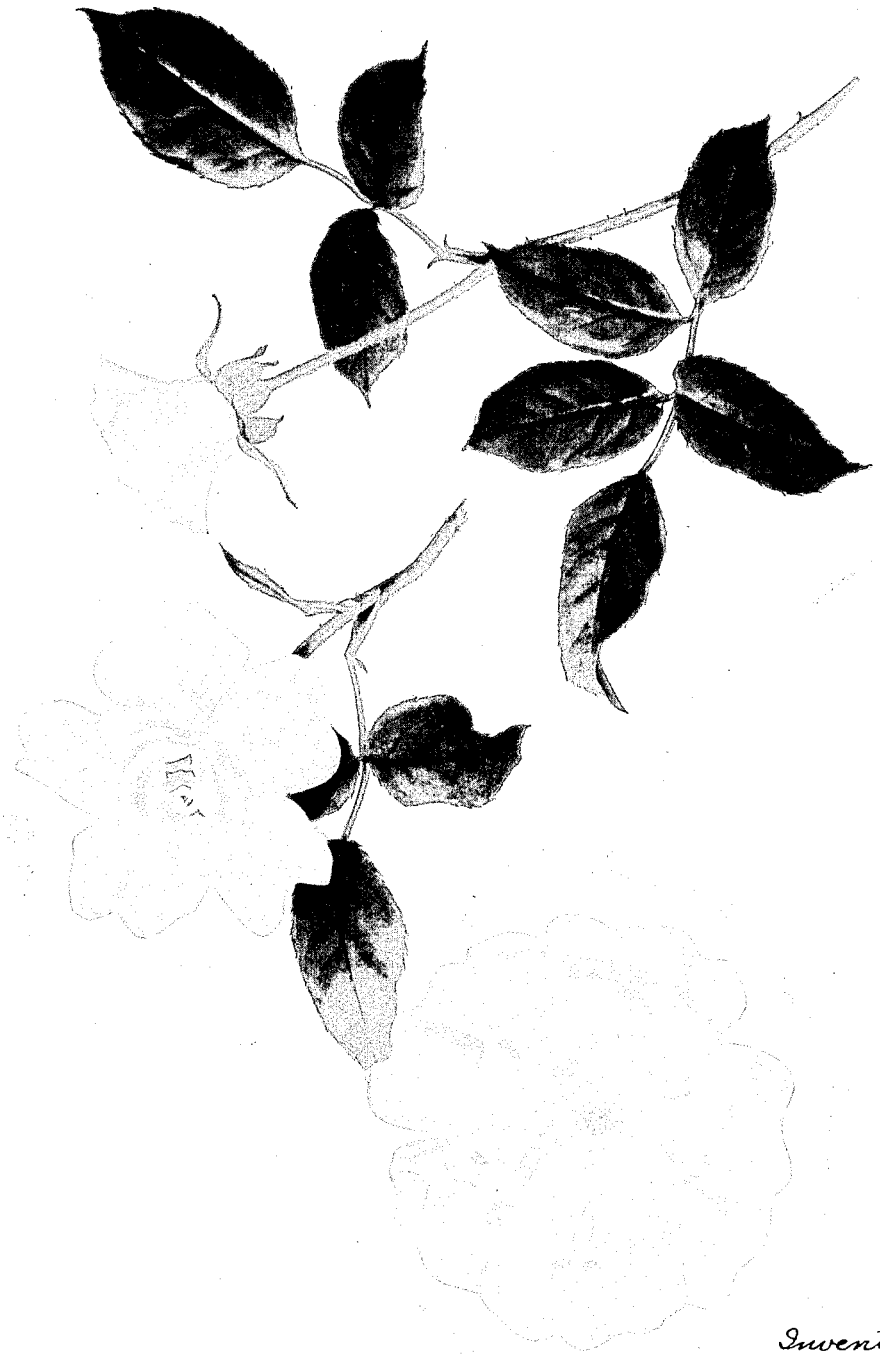
Inventor:
Walter Armacost
By: Robb & Robb
Attorneys.

Patented Feb. 6, 1945

Plant Pat. 649

UNITED STATES PATENT OFFICE

649

ROSE PLANT

Walter Armacost, West Los Angeles, Calif., assignor to Armacost & Royston, Inc., West Los Angeles, Calif., a corporation of California Application October 17, 1944, Serial No. 559,009

1 Claim. (Cl. 47—61)

The present invention relates to a new and distinct variety of rose plant, originating as a sport of the well-known variety "Rose Elfe."

The distinctiveness of the new variety may be most clearly explained by comparison thereof with its parent, from which it differs in a number of important respects. First, the color of the flowers is a pale vinaceous pink, whereas "Elfe" is much deeper, or specifically is deep rose pink. This distinguishing color will be clearly apparent by reference to the accompanying illustrations in which are shown a specimen of the new variety in the opening of the bud, partially blown and fully open stages of development, respectively, of the bloom.

Secondly, it differs in form of the bloom in that each and every petal of the new variety is serrated, a characteristic not appearing in the parent to any noticeable extent.

Thirdly, the stamens of the sport are a very distinct and beautiful feature of the half open and fully open rose, being very prominent and giving the effect of a wild rose, whereas in the parent the stamens are so short as not to be particularly noticeable.

Fourthly, the foliage, while similar in every other respect, is deep bronze in the young and half developed stages, whereas the parent foliage has red tips with scarcely a suggestion of bronze in any stage of growth.

Lastly, the keeping quality of this new rose is unusually good, this being generally apparent from the fact that it is marked by a vigorous habit of growth, free production of flowers throughout the whole year, and exceptionally long lasting quality thereof, as hereinafter more particularly specified.

Asexual reproduction of this new variety shows the foregoing characteristics come true to form and are established.

The following is a detailed description of the new variety, color terminology referring to dictionary definition, except where otherwise indicated by standard chart designation:

Type: Half hardy; bush; greenhouse; outdoor; sport; for cut flowers and garden decoration.
Class: Hybrid tea.
Discovery: At West Los Angeles, California.
*Parent.*—"Elfe."
Propagation: Holds its distinguishing characteristics through succeeding propagations by cuttings, grafting, budding and layering.

*Flower*

Locality where grown: West Los Angeles, California.
Flowers borne: Several to stem; in cluster; on normal, short stems.
Quantity of bloom: Abundant; outdoors; in greenhouse.
Continuity: Continuous.
Fragrance: Moderate; tea.
Bud:
*Peduncle.*—Short; medium heavy; erect; dark green; medium smooth; few red prickles.
*Before calyx breaks.*—*Size*—small. *Form*—globular with a conspicuous neck; with foliaceous appendages on the surface of the bud; with much-cut foliaceous parts extending beyond the tip of the bud equal to one-half to three-fourths or more of its length.
*As calyx breaks.*—*Color*—Pale Vinaceous Pink (Ridgway, Plate 27, F).
*As first petal opens.*—*Size*—small. *Form*—flat. *Color*—outside and inside—Pale Vinaceous Pink (Ridgway, Plate 27, F). Opening—opens up well in normal conditions; affected only by great extremes.
Bloom:
*Size.*—When fully open, small; 2 to 2½ inches.
*Petalage.*—Double; from 40 to 45 petals arranged irregularly.
*Form.*—Flat; becoming high centered; petals remaining at first rolled outward; becoming later, tightly rolled outward.
Petals: Thick; with inside and outside satiny.
*Shape.*—Outside—obovate; with one notch. Intermediate—obovate; with one notch. Inside—obovate; irregular, with many notches.
*Color.*—Colors may be modified by being shaded.

This description of a newly opened flower was made from a rose grown in a greenhouse in the month of September, 1944, at West Los Angeles, California:

*Color.*—*Outside petal*—outside surface: Pale Vinaceous Pink (Ridgway, Plate 27, F); inside surface: Pale Vinaceous Pink—shaded Vinaceous Pink (Ridgway, Plate 27, F). *Intermediate petal*—outside surface: Pale Vinaceous Pink—Shaded Vinaceous Pink; Amber Yellow at base (Ridgway, Plate 16, B); inside surface: Pale Vinaceous Pink—Veined Thulite Pink (Ridgway, Plate 26, A), with Amber Yellow base. *Inner petal*—outside surface: Pale Vinaceous Pink—Shaded Vinaceous Pink; inside surface: Vinaceous Shaded Rocellin Purple (Ridgway, Plate 38, B), with Amber Yellow base.

The following description was made from a rose that was open for three days in a greenhouse in the month of September, 1944, at West Los Angeles, California:

*Color.*—Outside and inside surfaces of the outside and inside petals same as above described in connection with newly opened flower.

*General color effect.*—Newly opened flower and three days open—same as described above.

*Behavior.*—Persist; fading brown; faded by heat.

*Flower longevity.*—Cut roses grown in greenhouse kept at living-room temperatures, ten days in November to March.

*Reproductive organs*

Stamens: Many; arranged regularly about pistils.
Filaments: Long; Yellow; with anthers.
Anthers: Medium size; Red; all open at once.
Pollen: Abundant; Yellow.
Pistils: Medium number.
Styles: Even; medium length; medium heavy; bunched.
Stigma: White.
Ovaries: All enclosed in calyx.
Hips: Short; globular; Green; moderately hairy; walls fleshy.
Sepals: Falling soon; moderately long; spear-shaped; recurved.

*Color.* — Inside — Gray - Green. Outside — Green.

Seeds: Many; medium size.

*Plant*

Foliage:

*Leaves.*—Compound of 5 to 7 leaflets; abundant; medium size; moderately heavy; glossy.

*Leaflets.*—Shape—Oval with apex acute; base acute; margin, serrate.

*Color.* — *Mature* — upper surface — Dark Green; under surface — Light Green. *Young* — upper surface — Bronze; under surface—Gray Bronze.

*Rachis (the supporting stem of the compound leaf).* — Medium heavy. Upper side — grooved; prickly. Under side — sparsely thorny.

*Stipules.*—Medium length; narrow; with medium length points, turning out at an angle of 90°.

*Disease.*—Resistant to mildew and blackspot insofar as this is evidenced by absence of any throughout development and establishing of this variety.

Growth:

*Habit.*—Bushy; much branched.

*Growth.*—Vigorous.

*Canes.*—Medium heavy.

*Branches.*—Green. *Thorns*—few; medium length; hooked downward; with broad base. *Prickles*—many; reddish. *Hairs*—many; reddish.

*New shoots.*—Red. *Thorns*—several; medium length; hooked downward; with long narrow base. *Prickles*—many; reddish. *Hairs*—many; Green.

I claim:

A new and distinct variety of rose plant, characterized as to novelty by the color of the flowers; matched form of each and every petal; prominence of the stamens in the half and fully open stages of development of the blooms, giving the effect of a wild rose; the deep bronze color of the foliage at said stages; free production of the flowers throughout the whole year and their exceptionally long lasting quality, substantially as shown and described.

WALTER ARMACOST.